United States Patent

Agouridas et al.

[11] Patent Number: 6,096,714
[45] Date of Patent: Aug. 1, 2000

[54] ERYTHROMYCIN DERIVATIVES, METHOD FOR PREPARING SAME, AND USE THEREOF AS DRUGS

[75] Inventors: Constantin Agouridas; Jean-Francois Chantot, both of Nogent Sur Marne, France

[73] Assignee: Hoechst Marion Roussel, France

[21] Appl. No.: 09/125,959

[22] PCT Filed: Feb. 27, 1997

[86] PCT No.: PCT/FR97/00351

§ 371 Date: Oct. 9, 1998

§ 102(e) Date: Oct. 9, 1998

[87] PCT Pub. No.: WO97/31929

PCT Pub. Date: Sep. 4, 1997

[30] Foreign Application Priority Data

Feb. 28, 1996 [FR] France .................. 96 02472

[51] Int. Cl.[7] .................................................. A61K 31/70
[52] U.S. Cl. ................. 514/29; 536/7.2; 536/7.4
[58] Field of Search ............... 514/29; 536/7.2, 536/7.4

[56] References Cited

U.S. PATENT DOCUMENTS 5,444,051  8/1995  Agouridas et al. ................. 514/29

FOREIGN PATENT DOCUMENTS 0487411  5/1992  European Pat. Off. .
0716093  6/1996  European Pat. Off. .

OTHER PUBLICATIONS

LeMahieu et al. *J. Med. Chem.* 1974, 17(9), 953–956.

*Primary Examiner*—Kathleen K. Fonda
*Attorney, Agent, or Firm*—Bierman, Muserlian and Lucas

[57] ABSTRACT

A subject of the invention is the compounds of formula (I):

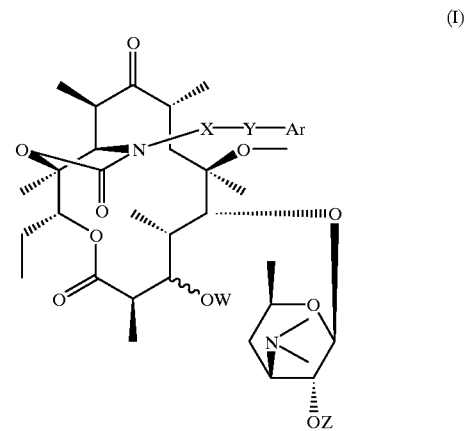

in which:
X represents a $CH_2$ or $SO_2$ radical or an oxygen atom, Y represents a $(CH_2)_m$—$(CH=CH)_n(CH_2)_o$ radical, with $m+n+o \leq 8$, $n=0$ or 1, Ar represents an aryl radical,
W represents a hydrogen atom, or the remainder of a carbamate function.

The compounds of formula (I) have useful antibiotic properties.

15 Claims, No Drawings

ERYTHROMYCIN DERIVATIVES, METHOD FOR PREPARING SAME, AND USE THEREOF AS DRUGS

This application is the U.S. national stage entry under 35 U.S.C. 371 of PCT/FR97/00351, filed Feb. 27, 1997.

The present invention relates to new erythromycin derivatives, their preparation process and their use as medicaments.

A subject of the invention is the compounds of formula (I):

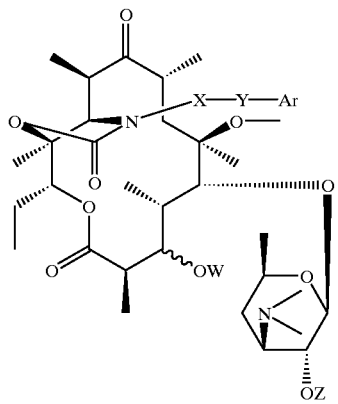

in which:

X represents a $CH_2$ or $SO_2$ radical or an oxygen atom, Y represents a $(CH_2)_m$—$(CH=CH)_n(CH_2)_o$ radical, with $m+n+o \leq 8$, $n=0$ or $1$, Ar represents an optionally substituted aryl radical, W represents a hydrogen atom, or the remainder of a carbamate function

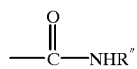

in which R" represents an alkyl radical containing up to 8 carbon atoms or an optionally substituted aryl radical, Z represents a hydrogen atom or the remainder of an acid, as well as their addition salts with acids.

Among the addition salts with acids, there can be can mentioned the salts formed with the following acids: acetic, propionic, trifluoroacetic, maleic, tartaric, methanesulphonic, benzenesulphonic, p-toluenesulphonic, and in particular stearic, ethylsuccinic or laurylsulphonic.

The aryl radical can be a phenyl or naphthyl radical.

The aryl radical can also be a substituted or non-substituted heterocyclic radical such as the thienyl, furyl, pyrolyl, thiazolyl, oxazolyl, imidazolyl, thiadiazolyl, pyrazolyl or isopyrazolyl radical, a pyridyl, pyrimidyl, pyridazinyl or pyrazinyl radical, or also an indolyl benzofurannyl, benzothiazyl or quinolinyl radical.

These aryl radicals can contain one or more groups chosen from the group constituted by hydroxyl radicals, halogen atoms, $NO_2$ radicals, $C\equiv N$ radicals, alkyl, alkenyl or alkynyl, O-alkyl, O-alkenyl or O-alkynyl, S-alkyl, S-alkenyl or S-alkynyl and N-alkyl, N-alkenyl or N-alkynyl radicals, containing up to 12 carbon atoms optionally substituted by one or more halogen atoms, the

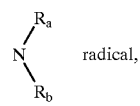

$R_a$ and $R_b$, identical or different, representing a hydrogen atom or an alkyl radical containing up to 12 carbon atoms, the

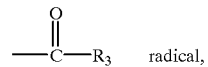

$R_3$ representing an alkyl radical containing up to 12 carbon atoms, or an optionally substituted aryl or heteroaryl radical, the following radicals: carboxylic aryl, O-aryl or S-aryl or heterocyclic aryl, O-aryl or S-aryl with 5 or 6 members containing one or more heteroatoms, optionally substituted by one or more of the substituents mentioned hereafter.

As preferred heterocycle, there can be mentioned among others:

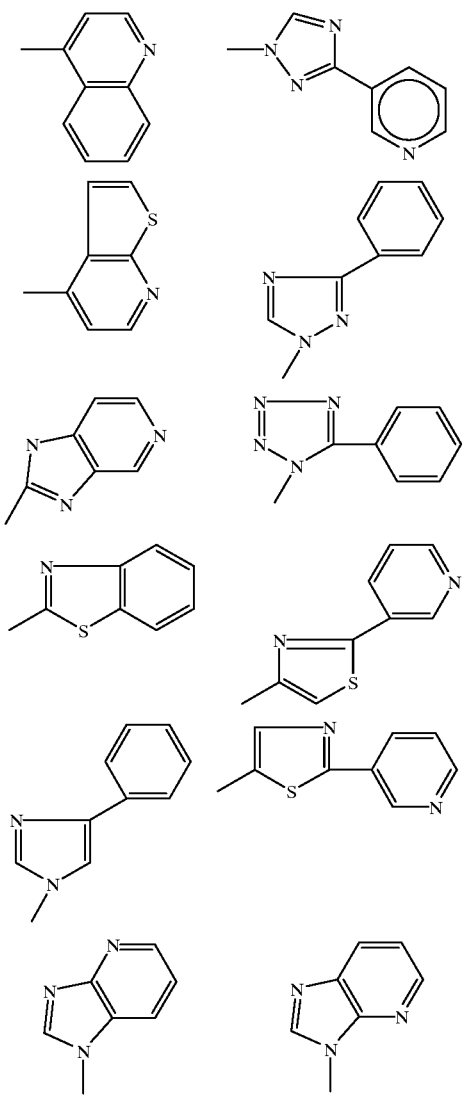

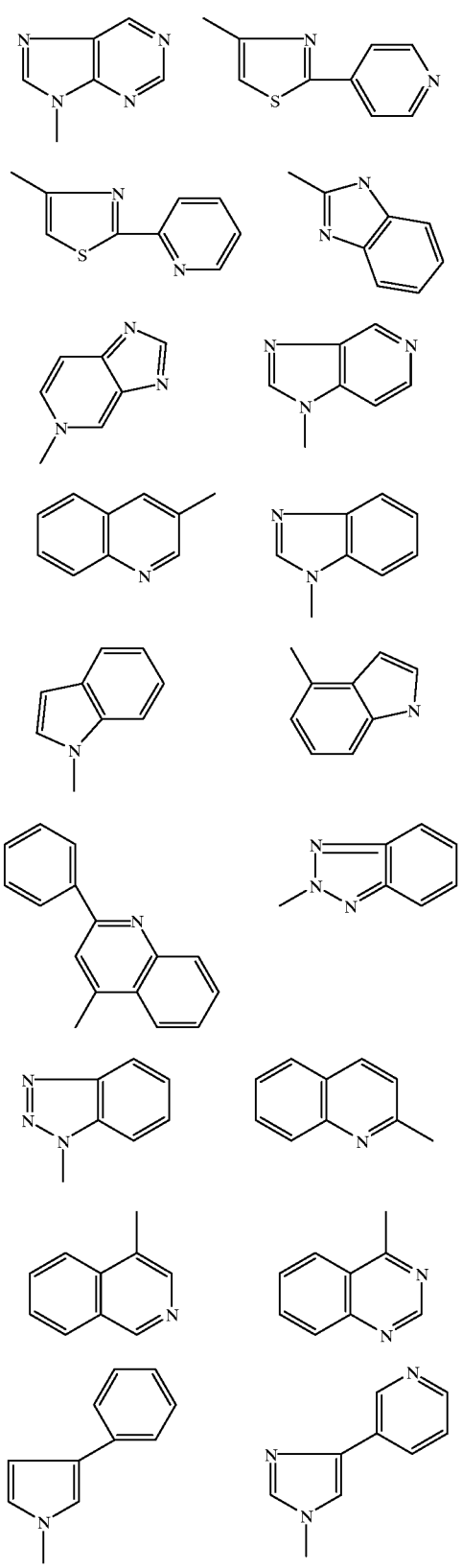
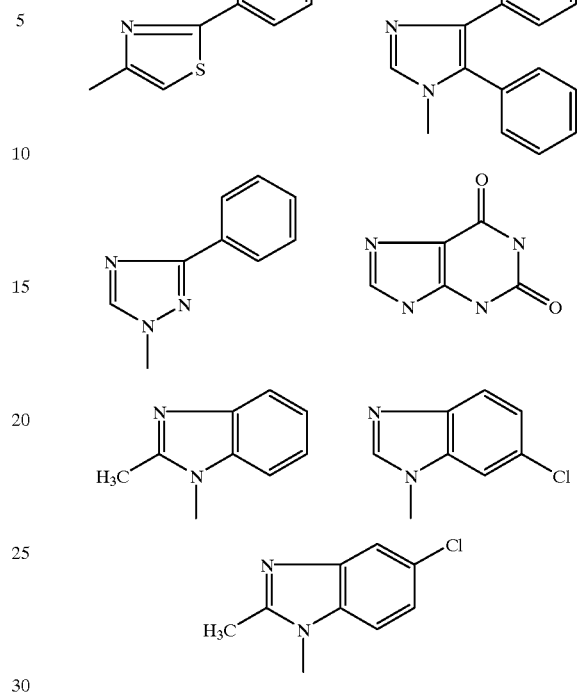

and the heterocyclic radicals envisaged in the European Patent Applications 487411, 596802, 676409 and 680967. These preferred heterocyclic radicals can be substituted by one or more functional groups.

A more particular subject of the invention is the compounds of formula (I) in which Z represents a hydrogen atom, those in which W represents a hydrogen atom, those in which X represents a $CH_2$ radical, those in which Y represents a $(CH_2)_3$, $(CH_2)_4$ or $(CH_2)_5$ radical.

Among the preferred compounds of the invention, there can be mentioned the compounds of formula (I), in which Ar represents a heterocyclic aryl radical, such as for example those in which Ar represents a 4-quinolinyl radical optionally mono- or polysubstituted on one and/or the other of the 2 quinoline rings, and quite particularly the compounds of formula (I) in which Ar represents a non-substituted 4-quinolinyl radical, or also for example the compounds of formula (I), in which Ar represents an optionally substituted:

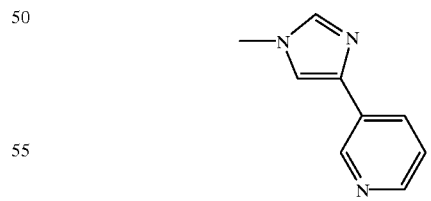

Among the preferred compounds of the invention, there can naturally be mentioned the products whose preparation is given hereafter in the experimental part.

The products of general formula (I) have a very good antibiotic activity on gram$^+$ bacteria such as staphylococci, streptococci, pneumococci.

The compounds of the invention can therefore be used as medicaments in the treatment of infections caused by susceptible germs and in particular, in that of staphylococcal infections, such as staphylococcal septicemias, malignant staphylococcal infections of the face or skin, pyodermatitis, septic or suppurating sores, boils, anthrax, phlegmons, erysipelas and acne, staphylococcia such as acute primary or post-influenzal angina, bronchopneumonia, pulmonary suppuration, streptococcal infections such as acute anginas, otitis, sinusitis, scarlet fever, pneumococcal infections such as pneumonia, bronchitis; brucellosis, diphtheria, gonococcal infection.

The products of the present invention are also active against infections caused by germs such as Haemophilus influenzae, Rickettsies, Mycoplasma pneumoniae, Chlamydia, Legionella, Ureaplasma, Toxoplasma or by germs of the Mycobacterium genus.

Therefore a subject of the present invention is, as medicaments and in particular antibiotic medicaments, the products of formula (I) as defined above, as well as their addition salts with pharmaceutically acceptable mineral or organic acids.

A more particular subject of the invention is, as medicaments and in particular antibiotic medicaments, the products of Examples 1 or 2 and their pharmaceutically acceptable salts.

A subject of the invention is also the pharmaceutical compositions containing at least one of the medicaments defined above as active ingredient.

These compositions can be administered by buccal, rectal, parenteral route or by local route as a topical application on the skin and mucous membranes, but the preferred administration route is the buccal route.

They can be solid or liquid and be presented in the pharmaceutical forms commonly used in human medicine, such as for example, plain or sugar-coated tablets, capsules, granules, suppositories, injectable preparations, ointments, creams, gels; they are prepared according to the usual methods. The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

These compositions can also be presented in the form of a powder intended to be dissolved extemporaneously in an appropriate vehicle, for example apyrogenic sterile water.

The dose administered is variable according to the illness treated, the patient in question, the administration route and the product considered. It can be, for example, comprised between 50 mg and 500 mg per day by oral route, for an adult for the product of Example 1 or Example 2.

A subject of the invention is also a preparation process, characterized in that a compound of formula (II):

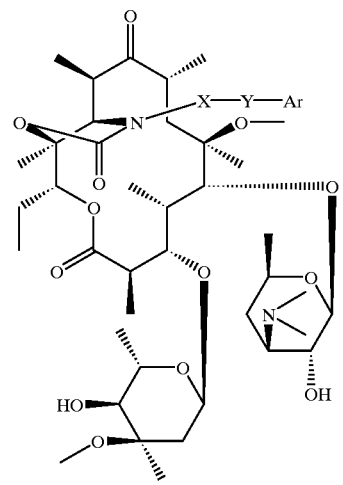

in which X, Y and Ar are as defined above, is subjected to the action of a cleavage agent of cladinose in order to obtain the corresponding compound of formula ($I_A$):

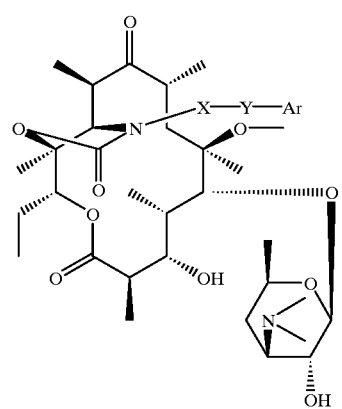

in which X, Y and Ar retain their previous meaning, which is subjected, if desired, to the action of an esterification agent or to the action of an agent capable of introducing the carbamate radical.

In a preferred implementation the cleavage of cladinose in position 3 is carried out using an acid.

The products of formula (II) used as starting products, are products which can be prepared according to the process described in the European Patent Application 076093 filed on Dec. 6, 1995 by the Company ROUSSEL UCLAF.

The products of formula (II) can be prepared according to a process characterized in that a compound of formula (III):

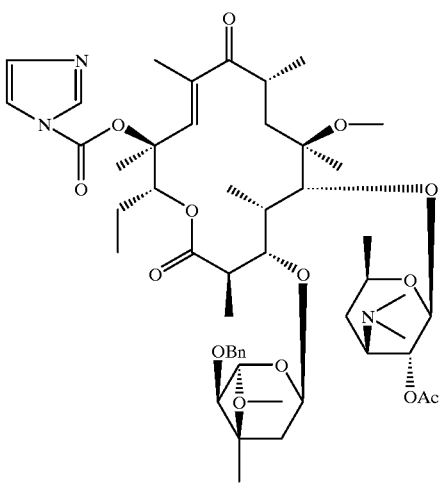

(III)

in which Bn represents a benzyloxycarbonyl radical and Ac an acyl radical containing 2 to 20 carbon atoms, is subjected to the action of a compound of formula (IV):

(IV)

in which $R_3$ represents the X—Y—Ar radical, X, Y and Ar being defined as previously in order to obtain the compound of formula (V):

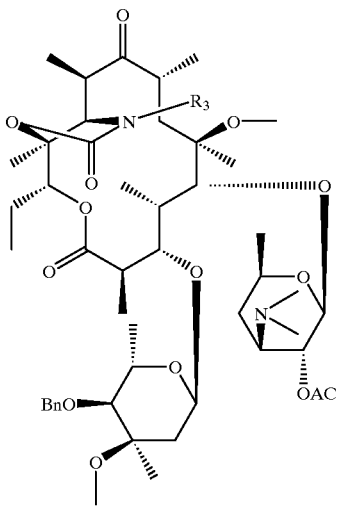

(V)

which is subjected, if desired, to the action of a cleavage agent of the ester function in position 2' in order to obtain the corresponding 2'—OH compound, then if desired, the compound thus obtained is subjected to the action of a reducing agent in order to carry out the cleavage of the benzyloxy carbonyl group in position 4" and to obtain the product of formula (II).

The compounds of formula (III) used as starting products are known products described in the European Patent 0,248,279.

The amines of formula (IV) are known in a general way and can be prepared according to the processes described in J. Med. Chem. (1982) Vol. 25, p. 947 and subsequent or also Tetrahedron Letters Vol. 32 No. 14, p. 1699, 1702 (1991).

The cleavage of the acetate in position 2" is carried out using methanol.

The cleavage of the benzyloxycarbonyl group in position 4" is carried out by reduction, for example using hydrogen in the presence of a palladium catalyst.

The salification is carried out using an acid according to standard processes.

The following examples illustrate the invention without however limiting it.

EXAMPLE 1

11,12-dideoxy-3-de((2,6-dideoxy-3-C-methyl-3-O-methyl-alpha-L-ribohexopyranosyl)oxy)-3-hydroxy-6-O-methyl-12,11-(oxycarbonyl(2-(3-(4-quinolinyl) propyl)hydrazono)) erythromycin 1 cm$^3$ of a solution of hydrochloric acid in ethanol (22 g/l) is added to a solution containing 250 mg of 11,12-dideoxy-6-O-methyl-12,11-(oxycarbonyl(2-(3-(4-quinolinyl)propyl) hydrazono) erythromycin. The reaction mixture is agitated at ambient temperature for one hour. It is poured into water, extracted with ethyl acetate, the aqueous phase is taken up, adjusted to a basic medium, extracted with ethyl acetate, dried, filtered and evaporated to dryness. In this way 271 mg of a product is obtained which is dissolved in ethyl acetate, then sulphuric ether is added until the product crystallizes. After washing with sulphuric ether, 169 mg is obtained which is recrystallized. After drying at 80° C., 120 mg of product melting at 166° C. is obtained.

The product 11,12-dideoxy-6-O-methyl-12,11-(oxycarbonyl(2-(3-(4-quinolinyl)propyl)hydrazono) erythromycin was prepared as follows:

STAGE A: Preparation of 11,12-dideoxy 6-O-methyl 12,11-(oxycarbonyl(2-hydrazono)) erythromycin (product P)

a) Condensation

A mixture of 3 g of 10,11-didehydro 11-deoxy 6-O-methyl erythromycin 2'-acetate 12-(1H-imidazole-1-carboxylate 4"-(phenylmethylcarbonate), 3 ml of hydrazine hydrate, 30 ml of acetonitrile and 492 mg of caesium carbonate is plunged in a bath at 80° C. for 10 mn, followed by concentrating to dryness, taking up in methylene chloride, washing with water, drying, filtering and bringing to dryness.

b) Deacetylation 3 g of the product obtained is dissolved in 30 ml of methanol and agitation is carried out at ambient temperature for 15 hours followed by concentrating to dryness. 2.7 g of deacetylated product is obtained.

c) Hydrogenolysis

The product obtained in Stage b) is dissolved in 100 ml of methanol. Hydrogenolysis is carried out in the presence of 600 mg of 10% palladium on activated charcoal, followed by filtering, rinsing with methanol and methylene chloride then the filtrate is concentrated to dryness. 2.52 g of a product is obtained which is purified by eluting with an isopropyl ether-methanol-triethylamine mixture (80-10-10). 941.8 mg of a product is obtained which is chromatographed again eluting with an isopropyl ether-methanol-triethylamine mixture (80-10-10). In this way 761 mg of 6-O-methyl-12,11-(oxycarbonyl) (2-hydrazono)) erythromycin is obtained.

| Microanalysis | Calculated | Found |
|---|---|---|
| C % | 59.45 | 58.8 |
| H % | 8.83 | 8.5 |
| N % | 5.33 | 5.2 |
| Mass spectrum | | |
| $788^+ = MH^+$ | | |
| $810^+ = MNa^+$ | | |

STAGE B: 11,12-dideoxy 6-O-methyl 12,11-(oxycarbonyl-(2-(3-(4-quinolinyl)propyl)hydrazono) erythromycin A mixture of 230 mg of the product obtained in Stage A above, 5 ml of methanol, 0.3 g of quinoline 4-propanal, 0.055 ml of acetic acid is agitated for 15 hours at ambient temperature. 0.065 g of sodium cyanoborohydride is added. Agitation is carried out at ambient temperature for 24 hours. The methanol is evaporated off, followed by extracting with ethyl acetate, washing with a soda solution then with water, drying, filtering and evaporating to dryness. 220 mg of a product is obtained which is chromatographed on silica, eluting with an ethyl acetate-triethylamine mixture (95-5). 80 mg of the sought product is obtained.

| Microanalysis | Calculated | Found |
|---|---|---|
| C % | 63.99 | 64.1 |
| H % | 8.42 | 8.3 |
| N % | 5.85 | 5.7 |
| Mass Spectrum | | |
| $158^+$ = OH in position 2' | | |
| $957^+ = (M^+H)^+$ | | |
| $979^+ = (M^+Na)^+$ | | |

EXAMPLE 2

11,12-dideoxy-3-de((2,6-dideoxy-3-C-methyl-3-O-methyl-alpha-L-ribohexopyranosyl) oxy)-3-hydroxy-6-O-methyl-12,11-(oxycarbonyl((4-(4-(3-pyridinyl)-1H-imidazol-1-yl)-butyl)imino))-erythromycin By operating as in Example 1 starting with 11,12-dideoxy-6-O-methyl-12,11-(oxycarbonyl((4-(4-(3-pyridinyl)-1H-imidazol-1-yl)butyl)imino))-erythromycin, the sought product was obtained. M.p.=210° C.

The starting product namely 11,12-dideoxy-6-O-methyl-12,11-(oxycarbonyl((4-(4-(3-pyridinyl)-1H-imidazol-1-yl)butyl)imino))-erythromycin was prepared according to the process indicated above for the preparation of the starting product of Example 1.

Example of Pharmaceutical Composition

Compounds were prepared containing:

| Product of Example 1 | 150 mg |
|---|---|
| Excipient s.q.f. | 1 g |

Detail of excipient: starch, talc, magnesium stearate

Pharmacological Study of the Products of the Invention

Method of Dilutions in Liquid Medium

A series of tubes were prepared into which the same quantity of sterile nutritive medium is distributed. Increasing quantities of the product to be studied are distributed into each tube, then each tube is seeded with a bacterial strain. After incubation for twenty-four hours in a heating chamber at 37° C., the growth inhibition is evaluated by transillumination, which permits the minimal inhibitory concentrations (M.I.C.) to be determined, expressed in micrograms/cm³.

The following results were obtained:

| GRAM+ bacterial strains | | |
|---|---|---|
| Products | Ex. 1 | Ex. 2 |
| Staphylococcus aureus 011UC4 | 0.3 | — |
| Staphylococcus aureus 011G025I | | |
| Staphylococcus epidermidis 012G011I | | |
| Streptococcus pyogenes group A 02A1UC1 | 0.04 | 0.15 |
| Streptococcus agalactiae group B 02B1HT1 | ≦0.02 | 0.04 |
| Streptococcus faecalis group D 02D2UC1 | 0.04 | 0.3 |
| Streptococcus faecium group D 02D3HT1 | 0.04 | 0.3 |
| Streptococcus sp group G 02G0GR5 | 0.04 | 0.15 |
| Streptococcus mitis 02mitCB1 | 0.3 | 0.04 |
| Streptococcus mitis 02mitGR16I | 0.15 | 0.6 |
| Streptococcus agalactiae group B 02B1SJ1 | 0.6 | 1.2 |
| Streptococcus pneumoniae 030SJ5 | 0.6 | 1 |

We claim:

1. A compound selected from the group consisting of

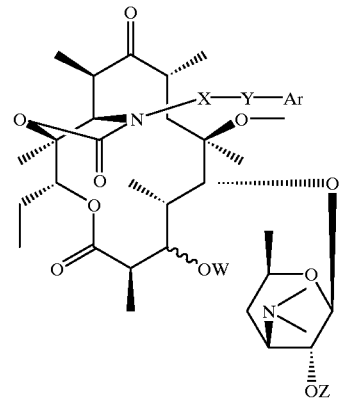

I wherein X is selected from the group consisting of —$CH_2$—, —$SO_2$— and —O—, Y is —$(CH_2)_m$—(CH=$CH_n$)—$(CH_2)_o$—, m+N+≦8, n is 0 or 1, Ar is aryl or heterocycle aryl, the aryl and heterocycle aryl being unsubstituted or substituted with at least one substituent selected from the group consisting of —OH, halogen, —$NO_2$, —CN, alkyl, alkenyl and alkynyl of up to 12 carbon atoms, optionally substituted with at least one halogen, alkylthio, alkenylthio and alkynylthio of up to 12 carbon atoms optionally substituted with at least one halogen, N-alkyl, N-alkenyl and N-alkynyl of up to 12 carbon atoms optionally substituted with at least one halogen,

and

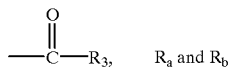

$R_a$ and $R_b$ are individually hydrogen or alkyl of 1 to 12 carbon atoms, $R_3$ is selected from the group consisting of 1 to 12 carbon atoms, aryl and heteroaryl, W is hydrogen or

R'' is alkyl of 1 to 8 carbon atoms or Ar is unsubstituted or substituted aryl, the substituents being at least one member of the group consisting of —OH, halogen, —NO$_2$, —CN, alkyl, alkenyl or alkynyl, O-alkyl, O-alkenyl, O-alkynyl, S-alkyl, S-alkenyl, S-alkynyl, N-alkyl, N-alkenyl and N-alkynyl containing up to 12 carbon atoms optionally substituted by at least one halogen, Z is hydrogen or acyl of an organic carboxylic acid and non-toxic, pharmaceutically acceptable acid addition salts of the compound of Formula I.

2. A compound of claim 1 selected from the group consisting of -11,12-dideoxy-3-de((2,6-dideoxy-3-C-methyl-3-O-methyl-alpha-L-ribohexopyranosyl) oxy)-3-hydroxy-6-O-methyl-12,11-(oxycarbonyl((4-(4-(3-pyridinyl)-1H-imidazol-1-yl)-butyl)imino))-erythromycin and -11,12-dideoxy-3-de((2,6-dideoxy-3-C-methyl-3-O-methyl-alpha-L-ribohexopyranosyl) oxy)-3-hydroxy-6-O-methyl-12,11-(oxycarbonyl(2-(3-(4-quinolinyl)propyl)hydrazono))-erythromycin.

3. Pharmaceutical compositions containing at least one medicament according to claim 1 as active ingredient.

4. A process for the preparation of a compound of claim 1 comprising reacting a compound of the formula

II

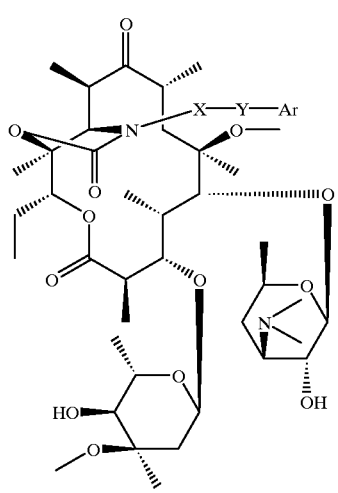

wherein X, Y and Ar are defined as in claim 1 with an acid to obtain a compound of the formula $I_A$

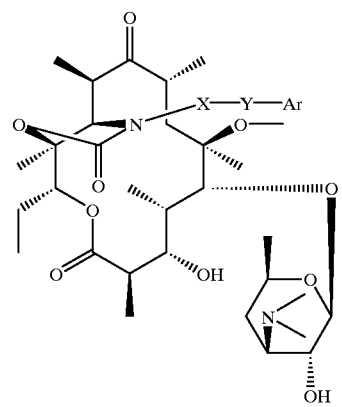

wherein X, Y and Ar are defined as above and optionally reacting the latter with an esterification agent or with an agent capable of introducing the carbamate radical.

5. A method of treating bacterial infections in a warm-blooded animal comprising administering to a warm-blooded animal a bactericidally effective amount of a compound of claim 1.

6. The method of claim 5 wherein the compound is selected from the group consisting of -11,12-dideoxy-3-de((2,6-dideoxy-3-C-methyl-3-O-methyl-alpha-L-ribohexopyranosyl) oxy)-3-hydroxy-6-O-methyl-12,11-(oxycarbonyl((4-(4-(3-pyridinyl)-1H-imidazol-1-yl)-butyl)imino))-erythromycin and -11,12-dideoxy-3-de((2,6-dideoxy-3-C-methyl-3-O-methyl-alpha-L-ribohexopyranosyl)oxy)-3-hydroxy-6-O-methyl-12,11-(oxycarbonyl(2-(3-(4-quinolinyl)propyl)hydrazono))-erythromycin.

7. A compound of claim 1 wherein Z is hydrogen.

8. A compound of claim 1 wherein w is hydrogen.

9. A compound of claim 1 wherein X is —CH$_2$.

10. A compound of claim 1 wherein Y is —(CH$_2$)$_n$ and n is 2 or 4 or 5.

11. A compound of claim 1 wherein Rr is heterocyclic-aryl.

12. A compound of claim 11 wherein Ar is 4-quinolinyl mono or polysubstituted.

13. A compound of claim 11 wherein Ar is unsubstituted 4-quinolinyl.

14. A compound of claim 1 wherein Ar is optionally substituted

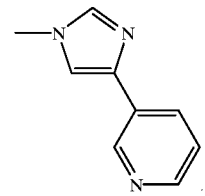

15. A bactericidally effective amount of a compound claim 1 and an inert pharmaceutical carrier.

* * * * *